(12) United States Patent
Obochi et al.

(10) Patent No.: US 6,659,107 B2
(45) Date of Patent: Dec. 9, 2003

(54) METHOD TO PREVENT XENOGRAFT TRANSPLANT REJECTION

(75) Inventors: Modestus O. K. Obochi, Vancouver (CA); Philippe Maria Clotaire Margaron, Burnaby (CA); Christopher Richard Honey, Vancouver (CA); Stephen Yip, West Vancouver (CA); Julia G. Levy, Vancouver (CA)

(73) Assignees: QLT Inc., Vancouver (CA); The University of British Columbia, Vancouver (CA)

( * ) Notice: Subject to any disclaimer, the term of this patent is extended or adjusted under 35 U.S.C. 154(b) by 0 days.

(21) Appl. No.: 10/099,755

(22) Filed: Mar. 14, 2002

(65) Prior Publication Data

US 2002/0139938 A1 Oct. 3, 2002

Related U.S. Application Data

(63) Continuation of application No. 09/169,233, filed on Oct. 9, 1998, now Pat. No. 6,364,907.

(51) Int. Cl.[7] .............................. A61B 19/00; A61F 2/02
(52) U.S. Cl. ..................... 128/898; 435/240.23; 623/66
(58) Field of Search ................................ 623/11.11, 66, 623/23.72, 23.76; 128/898; 435/240.23; 514/885, 908; 604/4.07, 500; 424/423, 427

(56) References Cited

U.S. PATENT DOCUMENTS

| | | | |
|---|---|---|---|
| 4,294,824 A | 10/1981 | Jones et al. | 424/101 |
| 4,696,286 A | 9/1987 | Cochrum | 128/1 R |
| 4,946,438 A | 8/1990 | Reemtsma et al. | 604/53 |
| 4,996,193 A | 2/1991 | Hewitt et al. | 514/11 |
| 5,135,915 A | 8/1992 | Czarniecki et al. | 514/21 |
| 5,171,749 A | 12/1992 | Levy et al. | 514/410 |
| 5,192,312 A | 3/1993 | Orton | 623/2 |
| 5,227,298 A | 7/1993 | Weber et al. | 435/178 |
| 5,422,362 A | 6/1995 | Vincent et al. | 514/410 |
| 5,824,080 A | 10/1998 | Lamuraglia | 424/423 |
| 5,880,145 A | 3/1999 | Sternberg et al. | 514/410 |
| 5,882,328 A | 3/1999 | Levy et al. | 604/20 |
| 5,929,105 A | 7/1999 | Sternberg et al. | 514/410 |
| 6,008,241 A | 12/1999 | Chan et al. | 514/410 |
| 6,364,907 B1 * | 4/2002 | Obochi et al. | 623/11.11 |

FOREIGN PATENT DOCUMENTS

| | | |
|---|---|---|
| JP | 60061501 | 4/1985 |
| WO | WO 96/21466 | 7/1996 |
| WO | WO 96/22090 | 7/1996 |
| WO | WO 97/11653 | 4/1997 |
| WO | WO 98/24476 | 6/1998 |
| WO | WO 98/52608 | 11/1998 |

OTHER PUBLICATIONS

The Economist (Mar. 22, 1997):99–101.
Aberer et al. J. Invest Dermatol. 76:202 (1981).
Barclay et al. "The Localization of Populations of Lymphocytes Defined by Monoclonal Antibodies in Rat Lymphoid Tissues" Immunology 42:593–600 (1981).
Bjorklund et al. "Intracerebral Grafting of Neuronal Cell Suspensions II. Survival and Growth of Niagral Cell Suspentions Implanted in Different Brain Sites" Acta Physiol Scand (Suppl) 522:9–18 (1983).
Borlongan et al. Neurological Res. 18:297–304 (1996).
Bowen et al. Lancet 2:585–586 (1979).
Brunden et al. "Cyclosporin A Increases Survival of Cross–species Intrastriatal Grafts of Embryonic Dopamine-containing Neurons" Experimental Brain Research 60:204–208 (1985).
Canti et al. Photochem Photobiol 34:589 (1981).
Deacon et al. Nature Medicine 3:350–353 (1997).
Dismore et al. Transplantation Proceedings 28:817–818 (1996).
Duan et al. Brain Res 712:119–212 (1996).
Elmeths et al. Cancer Res 46:1608 (1986).
Faustman et al. Proc. Natl. Acad. Sci. USA 78:5156 (1981).
Fishman. Neurobiol. 36:389–391 (1986).
Gibson et al. Brit J Cancer 69:473–481 (1994).
Gruner et al. Scand. J. Immunol. 21:267 (1985).
Hanau et al. J. Invest Dermatol 85:135 (1985).
Hill et al. Am J Otolaryngol 7:17–27 (1986).
Honey et al. Exp. Brain Res. 85:149–152 (1991).
Honey et al. Neuro Report 1:247–249 (1991).
Krutmann et al. J. Biol. Chem. 264:11407 (1989).
Lafferty et al. Science 188:259 (1975).
Lafferty et al. Transplantation 22:138–149 (1976).
Lau et al. Science 223:607 (1984).
Makino J Pediatric Surg 21:240–243 (1986).
Munro et al. "Biology of Disease: The Pathogenesis of Atherosclerosis: Atherogenesis and Inflammation" Laboratory Investigation 58(3):249–261 (1988).
Nelson et al. J NCI 80:56–60 (1988).
Obochi et al. Transplantation 63:810–817 (1997).
Okura. J Neurosci Res 48:385–396 (1997).
Pakzaban. Neuroscience 62:989–1001 (1994).
Pakzaban. Neuroscience 65:983–996 (1996).
Peng et al. Int. J. Cancer 46:719–729 (1990).
Pepino et al. Eur Surg Res 21:105–113 (1989).
Qin Transplantation 56:1481–1486 (1993).

(List continued on next page.)

Primary Examiner—David J. Isabella
(74) Attorney, Agent, or Firm—Morrison & Foerster LLP

(57) ABSTRACT

Donor material from a xenogeneic source is modified to enhance its survival time in a recipient by treating the donor material using low-dose photodynamic therapy (PDT). The donor material, such as an organ or cell suspension, is treated with a photosensitizer and irradiated in a low-dose protocol before transplantation into a xenogeneic recipient.

16 Claims, 2 Drawing Sheets

OTHER PUBLICATIONS

Richter et al. "Photosensitizing Efficiency of Two Regioisomers of the Benzoporphyrin Derivative Monoacid Ring A (BPD–MA)" Biochemical Pharmacology 43:2349–2358 (1992).

Ryba. Acta Neurologiae Experimentalis 55:259–270 (1995).

Sakai et al. Brain Res 565:167–170 (1991).

Shizuru. Transplantation 42:660 (1986).

Simkin et al. Proc Opt Method Tumor Treatment Detect, SPIE 2392:23 (1995).

Simon et al. J. Immunol. 146:485 (1991).

Sloan et al. Neuroscience 14:34–346 (1991).

Tang et al. J. Immunol. 146:3347 (1991).

Tang et al. J. Invest Dermatol. 99: 83 (1992).

White et al. Brit J Cancer 57:455–458 (Abstract) (1988).

Wood et al. Neuroscience 70:755–789 (1996).

Zhou et al. Brain Res 621:155–160 (1993).

\* cited by examiner

METHOD TO PREVENT XENOGRAFT TRANSPLANT REJECTION

This application is a continuation of U.S. patent application Ser. No. 09/169,233, filed Oct. 9, 1998, now U.S. Pat. No. 6,364,907, which is hereby incorporated by reference as if fully set forth.

TECHNICAL FIELD

The invention relates to the use of low-dose photodynamic therapy to modify donor tissue for xenograft transplantation. More particularly, it relates to exposing donor tissue intended for a recipient of a different species from the donor tissue to a photosensitizer and low intensity light.

BACKGROUND ART

PCT application publication no. WO96/21466 published Jul. 18, 1996, and incorporated herein by reference, describes a method for reducing the rejection of allografts by subjecting the donor tissue intended for an allograft recipient to low-light level photodynamic therapy. Skin allografts subjected to this treatment have enhanced survival times. Additional data demonstrating this effect are also described in U.S. Ser. No. 08/759,318 filed Dec. 2, 1996, and incorporated herein by reference. This work has also been reported by Obochi, M. O. K. et al., *Transplantation* (1997) 63:810–817.

These applications further mention that, in general, transplantation of tissue or organs is of three general types: syngeneic, where the donor tissue is of the same genotype as the recipient; allogeneic, wherein an allograft is derived from a donor of the same species as the recipient; and xenogeneic, where a xenograft is derived from a donor of a different species from the recipient. Transplantation using xenografts is of particular interest for use in human recipients since nonhuman donors can be used. However, model systems for such xenograft transplants can be constructed using two separate species of any derivations, such as rat/mouse, pig/bovine, and baboon/human.

Photodynamic therapy generally is a technique whereby a photosensitizer is administered directly to a tissue or organ or to a subject and the area desired to be treated is irradiated with light that is absorbed by the photosensitizer. In this state, the photosensitizer exerts an effect on the tissue or cells containing the photosensitizer. The effect may be cytotoxic or, alternatively, there may merely be an alteration in the function of the target cells or tissues. This approach has been used for selectively destroying tumor tissues, atherosclerotic plaques, the lesions of surface skin diseases, and unwanted pathogens in blood. Photodynamic therapy (PDT) has also been used to target activated cells of the immune system selectively.

Various effects of PDT on the immune system have been studied. It has been shown that photodynamic therapy using UV light, in particular 8-methoxypsoralen and UVA radiation, decreases 1 a antigens and the ATPase marker of epidermal Langerhans cells (LC) (Aberer, W. et al., *J Invest Dermatol* (1981) 76:202). The more standard photodynamic therapy combination of Photofrin® with visible light is able to inhibit APC from stimulating allogeneic cells in the MLR (Gruner, S. et al., *Scand J Immunol* (1985) 21:267). PDT with UVA light also inhibits upregulation of ICAM-1 expression by Langerhans cells (Tang, D. et al. *J Immunol* (1991) 146:3347). Photodynamic therapy using porphyrins inhibits the high affinity $F_c$-receptor on human monocytes (Krutmann, J. et al., *J Biol Chem* (1989) 264:11407).

Initially, PDT employed fairly high levels of radiation with the absorbed light. However, it has been shown that for certain applications, in particular modulating the immune system, only ambient light is necessary to activate the photosensitizer. Thus, "low-level" PDT is conducted at much lower intensities of irradiation than those required to obtain a recognized photodynamic effect, such as skin erythema. A detailed description of low-dosage PDT and its effect on the immune system is found in PCT application publication no. WO96/22090 published Jul. 25, 1996, and in U.S. Ser. No. 08/856,921 filed May 16, 1997. In general, the radiation levels in "low-dose PDT" have upper limits in the range of 100 mW/cm$^2$, more generally about 50 mW/cm$^2$ or 25 mW/cm$^2$ and lower intensities of less than 5 mW/cm$^2$, preferably less than 1 mW/cm$^2$ and more preferably less than 500 $\mu$W/cm$^2$ can also be used. Another criterion for radiation levels in low-dose PDT when an intact subject is administered low-dose PDT is that the light level used is less than one-quarter, preferably less than one-sixth, of that necessary to induce skin erythema in that subject. Still another measure of light dosage relates to total energy applied. Low-dose PDT employs energies of 10 J/cm$^2$ or less. The above-referenced applications describing treating of donor tissue for allograft transplantation describe the use of low-dose PDT for that purpose.

Xenografts are generally more at risk for rejection than allografts. Success in regard to a protocol that diminishes the immunogenicity of allografts is clearly not predictive of the success of that technique in diminishing the immunogenicity of xenografts to the extent required to ensure acceptance by the recipient. For example, PCT application no. WO97/11653 published Apr. 3, 1997, purports to describe a protocol using standard photodynamic therapy at conventional light dosage levels to treat both allografts and xenografts to enhance their acceptability to recipient subjects. However, this technique is demonstrated to be useful, if at all, only with respect to allografts. The work described employs phthalocyanine, preinjects the donor animals with this drug, applies levels of 5 $\mu$g/ml of the drug after explantation and during irradiation and supplies radiation at 100 mW/cm$^2$ for a total energy of 100 J/cm$^2$. Fluence at this level kills the cells in the graft. The subject tissue is an aortic graft; indeed, the applicants point out that their technique is applicable only to grafts comprising an extracellular matrix and an amorphous ground substance.

It does not appear that the technique described in PCT application no. WO 97/11653 would thus successfully be applied either to xenografts or to graft tissue which comprises cell suspensions per se, such as those ordinarily used to treat Parkinson's Disease. Other techniques known in the art also appear not to be sufficiently precise or successful to permit xenographic transplantation of neural tissue suspensions. Therefore, the source for replacement neural tissue in, for example, human patients with Parkinson's Disease has been human fetal neural tissue.

On a wider scale, there is only limited experience with interspecies transplantation of organs into humans. The shortage of donors for human patients in need of liver, ocular tissue, cardiac tissue, lungs, and the like is well known. To alleviate this shortage, it has been suggested that animals of another species be used as sources for these donor materials. There have been several reports attempting to evaluate the possibility of using nonhuman sources for transplants into the central nervous system. See, for example, Pakzaban, P. et al., *Neuroscience* (1994) 62:989–1001 which surveys the literature regarding neural xenotransplantation and editorials by Sloan, D. J. et al. *Neuroscience* (1991) 14:341–346, Fishman, P. S. *Neurobiol* (1986) 36:389–391 and in *The Economist* (Mar. 22, 1997):99–101. An additional summary is that by Borlongan, C. V. et al., *Neurological Res* (1996) 18:297–304.

Fetal pig dopaminergic neurons have been transplanted into 12 patients with Parkinson's; in one of these patients (who subsequently died), these neurons survived for at least 7 months (Deacon, T. et al., *Nature Medicine* (1997) 3:350–353). Attempts have also been made to modify the subject in whom the donor tissue will be implanted to become more receptive to the implant. For example, Honey, C. R. et al., *Exp Brain Res* (1991) 85:149–152 treated recipient murine subjects with monoclonal antibody against the murine equivalent of CD-4 (L3T4) and then provided them with rat-derived POA grafts, resulting in longer survival times of the transplants. Cyclosporin-A is a standard method to immunosuppress recipients of xenografts. Pepino, P. et al., *Eur Surg Res* (1989) 21:105–113 used photochemotherapy and ciclosporin [sic] in recipient baboons of heterotrophic heart grafts from the cynomolgus monkeys (*Macaca fascicularis*).

Other treatments of recipient animals for xenogeneic transplantation have been reported, including treatment with antibody to interleukin-2 receptor (Honey, C. R. et al., *Neuro Report* (1991) 1:247–249), with antibodies to T cell receptors (Wood, M. J. et al., *Neuroscience* (1996) 70:755–789), with antibodies to T cells per se (Okura, Y. et al., *J Neurosci Res* (1997) 48:385–396), with methyl prednisolone (Duan, W. et al., *Brain Res* (1996) 712:119–212), with FK506 (Sakai, K. et al., *Brain Res* (1991) 565:167–170), with 15-desoxyspergualin (Zhou, J. et al., *Brain Res* (1993) 621:155–160), and with 2-chlorodeoxyadenosine (Ryba, M. et al., *Acta Neurobiologiae Experimentalis* (1995) 55:259–270).

Thus, although PDT has been shown to inhibit the ability of lymphocytes to stimulate a mixed leukocyte reaction or to mediate graft host disease (Canti, G. et al., *Photochem Photobiol* (1981) 34:589) to inhibit the development of contact sensitivity in mice (Elmeths, C. A. et al., *Cancer Res* (1986) 46:1608; Simkin, G. et al., *Proc Opt Method Tumor Treatment Detect, SPIE* (1995) 2392:23) and to inhibit rejection of skin allografts (Quin, B. et al., *Transplantation* (1993) 56:1481). There has been no suggestion that photodynamic therapy or low-dose PDT can be used to treat xenogeneic donor material for transplantation into a subject of another species.

Donor tissue has been treated with UV light (Reemtsma et al., U.S. Pat. No. 4,946,438; Lau et al., *Science* (1984) 223:607). It has been suggested that UVB radiation may inhibit LC antigen-presenting cell function by preventing the expression of critical co-stimulatory molecules (Simon et al., *J Immunol* (1991) 146:485). Several authors have suggested that the exposure of LC to UVB or psoralen plus UVA radiation (PUVA) causes a loss of surface markers (including ATPase and class II MHC antigens) without causing overt cytotoxicity (Aberer et al, (1981, supra); Hanau et al, *J Invest Dermatol* (1985) 85:135). However, Tang and Udey (Tang et al., *J Invest Dermatol* (1992) 99:83) showed that the levels of UV radiation that inhibited LC accessory cell function and selectively modulated ICAM-1 expression in short-term cultures were ultimately cytotoxic for LC.

Sometimes UV light has been used in conjunction with microencapsulation (Weber et al., U.S. Pat. No. 5,227,298). Other workers have used barrier membranes alone, such as the bilayer comprising a first non-cytotoxic layer and a second outer layer of a biocompatible and semipermeable polymeric material taught by Cochrum, U.S. Pat. No. 4,696,286.

Donor tissue has been treated with a wide variety of substances, such as the topical application of cyclosporin to skin grafts, as disclosed by Hewitt et al., U.S. Pat. No. 4,996,193, and the perfusion of a donor kidney with lymphocytic chalone, as described by Jones et al., U.S. Pat. No. 4,294,824. The survival time of skin grafts has been prolonged by treatment in vitro with cortisone, thalidomide, or urethane before implantation into a laboratory animal. The amount of drug locally applied to the skin is usually smaller than the amount required to achieve a similar effect by injecting the drug systemically into the recipient. Donor skin has been treated in vitro with streptokinase/streptodornase, RNA and DNA preparations of the recipient, or solutions of glutaraldehyde, prior to transplantation to reduce the antigenicity of the skin to be grafted.

More sophisticated approaches have involved the treatment of donor tissue with a monoclonal antibody directed against the MHC product along with complement (Faustman et al., *Proc Natl Acad Sci USA* (1981) 78:5156) or the treatment of donor tissue with an immunoconjugate of antibody directed against the MHC (Shizuru, et al., *Transplantation* (1986) 42:660). Variable results were obtained by these methods.

For example, treatment of donor tissue has employed antibodies which mask the donor MHCI antigens (Pakzaban, P. et al., *Neuroscience* (1996) 65:983–996; Dismore, J. H. et al., *Transplantation Proceedings* (1996) 28:817–818). Extended time culturing of the donor tissue has also been suggested (Lafferty et al., *Science* (1975)188:259; Lafferty et al., *Transplantation* (1976)22:138–49; Bowen et al., *Lancet* (1979)2:585–86). Donor tissue has been treated with growth factor, such as TGF-beta (Czarniecki et al., U.S. Pat. No. 5,135,915), sometimes in combination with extended culture times (Orton, U.S. Pat. No. 5,192,312).

The use of PDT with xenografts appears to have been focused on exploration of PDT as a treatment for tumors. These studies employed in model systems, typically wherein human tumor tissue has been transplanted into immunodeficient mice. These studies do not relate to prolonging survival of the xenograft in the host. See, e.g., Gibson, S. L. et al. *Brit J Cancer* (1994) 69:473–481; Nelson, J. S. et al. *J NCI* (1988) 80:56–60; White, L. et al. *Brit J Cancer* (1988) 57:455–458; Makino, *J Pediatric Surg* (1986) 21:240–243; and Hill, J. H. et al. *Am J Otolaryngol* (1986) 7:17–27.

DISCLOSURE OF THE INVENTION

Despite the success of the use of low-dose photodynamic therapy in treating donor allografts, the enhanced difficulty of using cross-species donors for transplantation renders it surprising that this approach is also suitable for xenotransplantation. The difficulty in providing xenografts that will be accepted by the donor is well understood. While allograft tissue is clearly more at risk for rejection than syngeneic transplants, the quantum leap of species differences encountered when xenografts are substituted for allografts clearly distinguishes the behavior of these two types of donor tissues when ultimately transplanted into the recipient.

The present invention is directed to the use of low-dose photodynamic therapy to prevent rejection of donor xenogeneic tissue by modifying the tissue so as to reduce immunogenicity. In this approach, donor tissue is incubated with a suitable photosensitizer and then exposed to light of low intensity. After this treatment, the donor tissue is implanted into a xenogeneic recipient.

MODES OF CARRYING OUT THE INVENTION

Figure 1A:
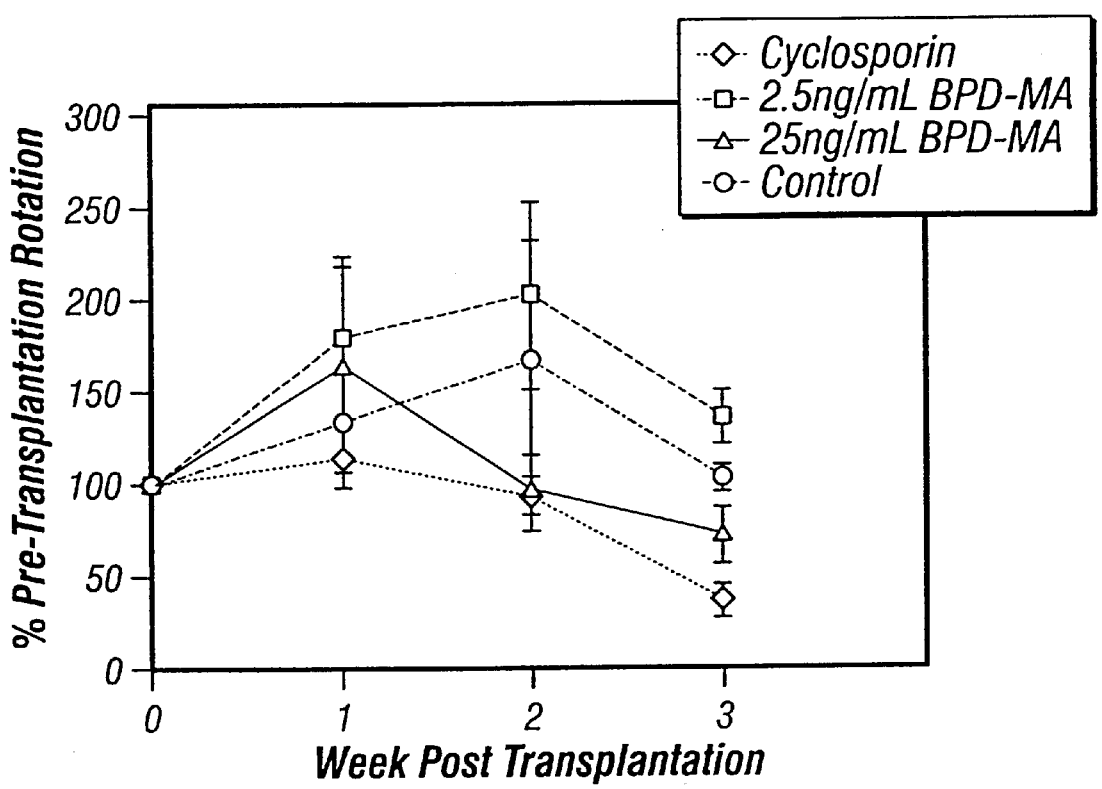
FIG. 1A is a graph showing the rotational behavior of neural tissue recipients over a three-week period.

The survival of transplanted tissue and organs can be significantly enhanced by treatment of the donor tissue with low-dose PDT. Although this treatment has been successful in the past in allograft transplantations, the present invention extends this efficacy to xenotransplants.

By "low-dose PDT" is meant a total photodynamic therapy experience at substantially lower levels of intensity than that ordinarily employed. Generally, there are three significant variables—the concentration of the photosensitizing drug, the intensity of the radiation employed and the time of exposure to light, which determines the total amount of energy ultimately delivered to the transplant tissue. Generally, an increase in one of these factors permits a decrease in the others. For example, if it is desired to irradiate only for a short period of time, as would be the case for a cell suspension in order to maintain viability, the energy of irradiation may be increased or the concentration of the drug may be increased. Conversely, if longer time periods of irradiation are permitted, lower irradiation intensities and lower drug concentrations are desirable. As exemplified below, the combination of 25 ng/ml as a drug concentration, 40 mW/cm$^2$ intensity and 10 J/cm$^2$ total radiation from an LED source provided successful results. This is in contrast to the protocol employed in PCT application WO 97/11653 in which a drug concentration of 5 $\mu$g/ml was combined with an intensity of 100 mW/cm$^2$ and a total energy delivered of 100 J/cm$^2$.

It is understood that the manipulation of these parameters will vary according to the nature of the donor tissue being treated and the nature of the drug employed. However, in general, low-dose PDT employs combinations of the drug concentration, intensity, and total energy values which are several fold lower than those conventionally used. One measure might be the product of concentration (e.g., in ng/ml)×intensity (e.g., in mW/cm$^2$)×time (e.g., in seconds). However, it is difficult to set absolute numbers for this product since there are constraints on each of the parameters individually. For example, if the intensity is too low, the photosensitizer will not be activated consistently; if the intensity is too high, hyperthermic and other damaging effects may occur. Similarly, drug concentrations cannot vary over any arbitrary range. There may also be constraints on the time during which radiation can be administered. Accordingly, the product of the foregoing equation is only a rough measure. However, this approach may provide a convenient index that can be adjusted according to the relative potency of the drug employed, and in general, an increase in intensity would permit a decrease in time of irradiation, and so forth.

The probable largest practical application of this invention is in the use of nonhuman donor tissue for transplantation into humans. However, any interspecies transplantation may utilize this technique as well. The nature of the donor tissue is of great variety, including, for example, complete organs such as heart, lung, liver, and the like; the nature of the donor organs depends on the available technical surgical skills; general tissues such as skin, neural tissue, bone marrow and the like; again, the nature of the donor tissue depends on the current technology in medicine generally; and, thus, any desired and practicable materials that will be helpful to the recipient if used to replace a corresponding defective organ or tissue in the recipient are included. As illustrated herein, in addition to organs and intact tissues, it may be useful to implant into recipients dissociated tissues in the form of cell suspensions. Typically, such suspensions comprise individual cells as well as clumps of these cells—i.e., the suspensions may be simply individual cell suspensions or may contain aggregates. Cellular suspensions are particularly useful when the donor material is, for example, neural tissue, pancreatic islets, or bone marrow cells. Separated enriched cell cultures may also be used.

For human recipients, donors from closely related species, such as other primates, including baboons has been attempted. However, more distant donors, such as porcine donors have been suggested. While these are the most commonly contemplated sources for organs and tissues, the thinking has been constrained by the almost certain rejection of the transplanted material by the recipient. Thus, given the success of the invention method in reducing immunogenicity and rejection, other sources such as ovine, bovine, and other mammalian species may also be considered. With respect simply to tissue, where the dimensions of the organ are not at issue, additional donor species for humans may also be envisioned, even avian species.

Similarly, veterinary uses of the technique of the invention are contemplated, as well as uses in animal research models, such as murine or rat models for human diseases and tumors.

According to the method of the invention, the donor organ or tissue is first incubated in the presence of a photosensitizing agent. In the case of an organ, profusion with a solution containing the photosensitizer may be desirable or required. For other tissues, such as skin grafts or for cells in suspension, simple incubation may suffice. Suitable photosensitizing agents are of a wide variety, including, without limitation, porphyrin related compounds such as hematoporphyrin derivative, Photofrin® porfimer sodium, the green porphyrins such as the BPDs, purpurins, chlorins, fluorins, etiopurpurins, and the like as well as phthalocyanines, pheophorbides, deuteroporphyrins, texaphrin, and the like. Particularly preferred photosensitizers are the green porphyrins, and in particular BPD-MA, EA6, and B3. Of course, combinations of photosensitizers may also be used. It is preferred that the absorption spectrum of the photosensitizer be in the visible range, typically between 350 nm and 1200 nm, more preferably between 400–900 nm, and even more preferably between 600–900 nm.

BPD-MA is described, for example, in U.S. Pat. No. 5,171,749; EA6 and B3 are described in U.S. Ser. Nos. 09/088,524 and 08/918,840, respectively, all incorporated herein by reference. Preferred green porphyrins have the basic structure:

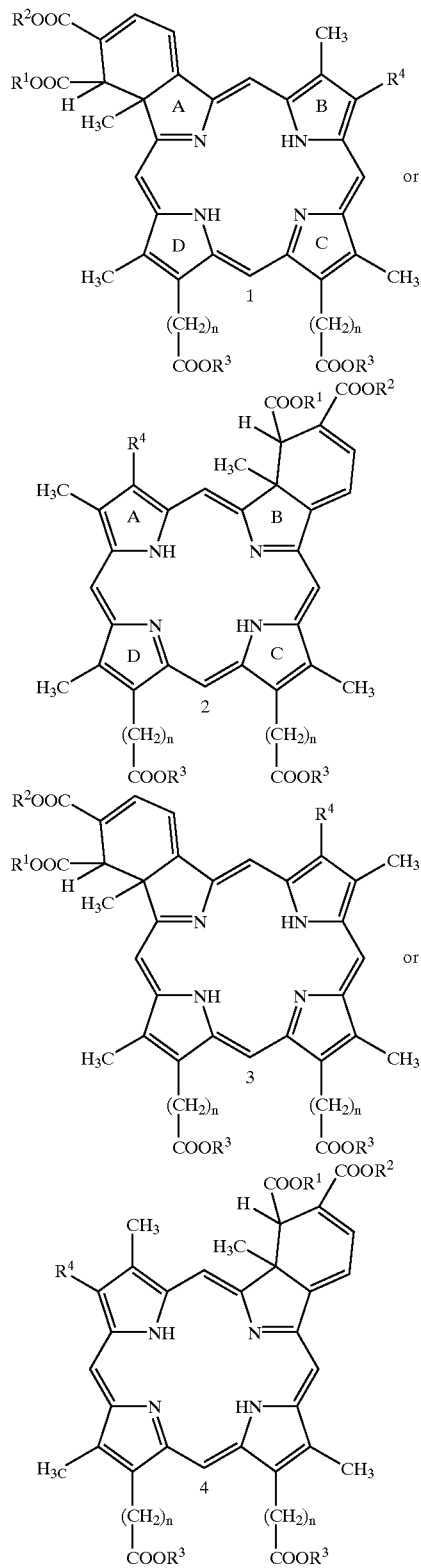

where $R^4$ is vinyl or 1-hydroxyethyl and $R^1$, $R^2$, and $R^3$ are H or alkyl or substituted alkyl.

BPD-MA has the structure shown in FIG. 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

Related compounds of formulas 3 and 4 are also useful; in general, $R^4$ will be vinyl or 1-hydroxyethyl and $R^1$, $R^2$, and $R^3$ are H or alkyl or substituted alkyl.

As indicated above, attaining a low-dose PDT protocol depends on the balance of the concentration of photosensitizer employed, light intensity, and time of irradiation which determines total energy. The values set forth hereinbelow for these parameters indicates the range in which they may be varied; however, the upper ranges of one parameter may mandate lower ranges of another.

The concentration of the photosensitizer in the incubating formulation will depend on the nature of the organ or tissue to be treated, the manner in which the formulation is contacted with the donor material, and the nature of the photosensitizer. Typical concentrations, however, are in the range of 1 ng/ml–10 µg/ml, preferably 2 ng/ml–1 µg/ml, and typically in the range of 10 ng/ml–100 ng/ml. However, these values are 1 µg/ml, and typically in the range of 10 ng/ml–100 ng/ml. However, these values are merely suggestions and may not apply to all of the photosensitizers. Optimizing the concentration of a particular photosensitizer is routinely practiced.

The additional components in the formulation used to treat the donor material are also dependent on the nature of the photosensitizer and the nature of the material to be treated. The formulation may be a liposomal formulation, an emulsion, or simply an aqueous solution. Buffers and other excipients may also be added. Gelling agents and other excipients may also be employed.

The time of treatment with photosensitizer is also variable depending on the nature of the components of the system, but typically an incubation time of 5 minutes-1 hour is sufficient. The incubation may occur in the dark and subsequent radiation supplied, or low-level light may be supplied during the incubation with photosensitizer.

The irradiation levels will be in the range generally employed for low-light-dose photodynamic therapy as described hereinabove. These typical levels are in the range of less than 100 mW/cm$^2$, preferably less than 50 mW/cm$^2$, more preferably less than 25 mW/cm$^2$ or less than 10 mW/cm$^2$ or less. A total dosage of 10 J/cm$^2$ or less is preferred. The light can be supplied by any convenient source using a wavelength absorbed by the photosensitizer chosen.

After the donor material has been contacted with photosensitizer and exposed to light, it can be stored for as long as about 24–48 hours. Preferably, however, it is used immediately in a transplant procedure. Storage life can be enhanced by using a blood substitute in the formulation of photosensitizer (e.g., a perfluorochemical emulsion), or using a formulation containing chilled isotonic agent and anticoagulant, followed by glycerol, to allow for the freezing of donor material with little destruction of the cells, as described in JP 60061501 published Apr. 9, 1985. In addition, the donor material can be preserved with different liquids that include the photosensitizer formulation while the organs are being cooled to freezing temperatures, to preserve the organ semi-permanently without cell necrocytosis.

Before transplantation, the graft is preferably washed free of the photosensitizing agent composition, for example, by soaking it in a physiological saline solution or by other means appropriate for this purpose. Also, prior to transplantation, the recipient may be given one or more donor-specific blood transfusions with PDT-treated peripheral blood mononuclear cells to aid in transplant survival. An alternative procedure is to subject the recipient to total lymphoid irradiation prior to the transplantation operation. Any other pre-transplant procedures that would be beneficial to the particular transplant recipient can be performed as part of the method of this invention.

In some instances, it is desirable to modify the surface of a graft so as to provide positively or negatively charged groups, as by using a suitable amino acid or polymer or by attaching a physiologically acceptable source of charged functional groups. For example, a negatively charged surface is appropriate for blood vessels to diminish blood clotting. It also is desirable in certain circumstances to render the surface hydrophobic or hydrophilic by coupling, e.g., phenylalanine, serine, or lysine, to the surface. An immunosuppressive agent particularly effective for these surface modifications is glutaraldehyde.

The transplantation procedure itself will depend on the particular disorder being treated, the condition of the patient or other animal subject, and the like. The practitioner will recognize the appropriate procedure to use in any given case. The transplants are optionally monitored systematically during the critical post-operative period (the first three months) using any suitable procedure, such as radionuclide intravenous angiography. After the transplantation, immunosuppression therapy, using an appropriate immunosuppressant may also be used.

The method of the invention can be supplemented by or used in combination with the same or reduced dosages of immunosuppressive agent simultaneously administered to the donor systemically, the donor tissue in vitro, or to the recipient, either locally or systemically. The term "immunosuppressive agent" as used herein refers to substances that act to suppress or mask the immune system of the host into which the graft is being transplanted. This would include substances that suppress cytokine production, down-regulate or suppress self-antigen expression, or mask the MHC antigens.

Examples of such agents include 2-amino-6-aryl-5-substituted pyrimidines; azathioprine or cyclophosphamide; bromocryptine; glutaraldehyde; antiidiotypic antibodies for MHC antigens; cyclosporin A; one or more steroids, preferably corticosteroids and glucocorticosteroids such as prednisone, methyl prednisolone, and dexamethasone; anti-interferon-gamma antibodies; anti-tumor necrosis factor-alpha antibodies; anti-tumor necrosis factor-beta antibodies; anti-interleukin-2 antibodies; anticytokine receptor antibodies such as anti-IL-2 receptor antibodies; heterologous anti-lymphocyte globulin; pan-T antibodies, preferably OKT-3 monoclonal antibodies; antibodies to CD4; streptokinase; streptodornase; or RNA or DNA from the host.

An effective amount, which is determined by these considerations, is the minimum amount necessary to prevent an immune response that would result in rejection of the graft by the recipient, but as much as necessary to achieve a longer graft survival time. Such amount is preferably below the amount that is toxic to the recipient or renders the recipient significantly more susceptible to infections. The amount of immunosuppressive agent required for the invention is typically lower than that normally required for transplanted grafts that have not been pre-treated, and depends on the individual circumstances surrounding the transplant and the type of immunosuppressive agent being used.

The following examples are intended to illustrate but not to limit the invention.

EXAMPLE 1

Preparation of a Neural Xenograft

A. Neural cells were prepared from fetal mice (crown-rump length 10–12 mm) as described by Brundin, P. et al. *Exp Brain Res* (1985) 60:204–208 by dissecting out the ventral mesencephalon and making a cell suspension, which contains individual cells as well as clumps of cells. Briefly, fragments of mesencephalon were incubated in 0.1% trypsin for 20 min at 37° C., washed 4 times in medium (RPMI+ 0.004% DNAse+0.0125% soybean antitrypsin+15 mM $MgSO_4$) and resuspended in 100 ml medium and triturated through a Pasteur pipette. Cell viability of the suspension was estimated with Trypan Blue exclusion. Viability was greater than $1\times10^7$/ml.

The suspension was incubated for 30 min at 37° C. in the dark with the following solutions:

| Group I:   | 2.5 ng/ml BPD-MA; |
| Group II:  | 25 ng/ml BPD-MA;  |
| Group III: | vehicle only;     |
| Group IV:  | vehicle only.     |

The BPD-MA was supplied by QLT PhotoTherapeutics, Inc. (Vancouver, B.C.) as liposomally formulated at 2 mg/ml in PBS. See Richter, A. M. et al. *Biochem Pharmacol* (1992) 43:2349.

The suspension was then exposed to 10 $J/cm^2$ of radiation from an LED source (690 nm±10 nm). The light source was LED BOX VER2 (QLT PhotoTherapeutics, Inc., Vancouver) consisting of a single panel of light-emitting diodes composed of 1280 LED. Peak wavelength was 696 nm and full-width spectrum at one-half maximum was 25 nm. The intensity of the panel was adjusted to 40 $mW/cm^2$.

B. The procedure set forth in paragraph A of this example was repeated, again using four groups of fetal mice but at higher concentrations of BPD-MA; Group I was treated with 25 ng/ml BPD-MA and Group II with 100 ng/ml BPD-MA.

EXAMPLE 2

Transplantation into Xenogeneic Recipients

The recipients were adult male Wistar Rats (200–250 g). The rats were housed in groups of 3–4 on a 12-hour light/dark cycle with free access to food and water. Under sodium pentobarbital anesthesia (15 mg/kg i.p.) the rats were placed in a stereotaxic frame with the incisor bar positioned 2.3 mm before the interaural line. The animals were injected with 6-hydroxydopamine HCl (8 mg in 4 ml saline with 0.02% ascorbate over 8 min) into the right median forebrain bundle by means of a Harvard infusion pump. Injections were placed −4.4 mm anterior to the bregma, 1.0 mm right of the midline and −7.8 mm from the dura as described by Bjorklund, A. et al. *Acta Physiol Scand* (Suppl.) (1983) 522:9–18.

Three weeks later, circling behavior in response to 2.5 mg/kg methamphetamine (s.c.) was quantified in automated rotometers. Total ipseversive rotations (360°) were counted for each animal over 1 hr and only animals rotating more than 6 turns/min were used as recipients. The rats were divided into four groups of 6 each so that each group had the same mean rotational scores.

Each rat received two 3 ml injections of one of the cell suspensions prepared in Example 1, paragraph A or paragraph B thereof, into the dopamine denervated striatum (coordinates with incisor bar at −2.3 mm were: 1.0 mm anterior to the bregma, 2.8 mm lateral to midline, 5.0 and 4.1 mm deep to dura). In addition, Group III in each case received daily intraperitoneal injections of 10 mg/kg cyclosporin A during the study.

EXAMPLE 3

Evaluation of Xenotransplanted Recipients

Over the three-week period subsequent to transplantation, the rotational behavior of the recipients was evaluated. The results are shown in FIGS. 1 and 2.

Figure 1B:
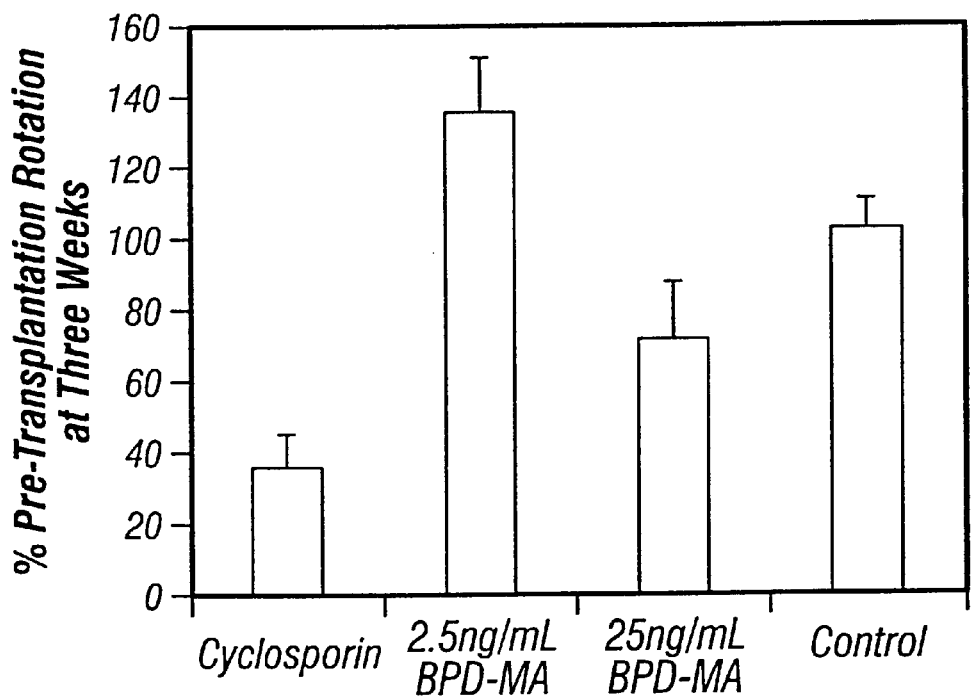
FIG. 1B shows a graphic representation of the rotational behavior of various groups at the 3-week end point.

FIG. 1A shows the results obtained when the recipients were injected with donor tissue treated as in Example 1, paragraph A. Solid squares represent Group I (2.5 ng/ml BPD-MA), closed triangles represent Group II (25 ng/ml BPD-MA), solid diamonds represent Group III (cyclosporin A), and open circles represent Group IV (control). After three weeks, the cyclosporin-treated animals (Group III) had significantly reduced rotation as compared to controls (Group IV), and although there was a trend for lower rotation in Group II (25 ng/ml BPD) there was no significant difference from Group IV. FIG. 1B shows the one time point at the end of the experiment 3 weeks post-transplantation in graphic form. As seen, 2.5 ng/ml BPD-MA resulted in recipients with rotational behavior somewhat higher than control; 25 ng/ml BPD-MA provided some improvement.

The rats were sacrificed three weeks subsequent to transplantation under anesthesia, perfused with intracardiac heparinized saline, and their brains removed and quick-frozen in OCT embedding compound (Miles, Ind., USA). Twelve-micron cryostat sections were prepared for indirect immunohistochemistry by the technique of Barclay, A. N. et al. *Immunol* (1981) 42:593–600. These sections were treated with primary antibody MCAO (Serotec®) against the Thy-1.2 antigen found on murine CNS neurons. A secondary antibody, AACO7P (Serotec®) coupled to horseradish peroxidase was stained with diaminobenzidine and counterstained with cresyl violet.

Examination of the sections showed that rats treated daily with cyclosporin (Group III) had surviving xenografts at 3 weeks; four of six animals whose xenografts were treated with 25 ng/ml BPD (Group II) had surviving xenografts. However, none of the animals in Group IV or in Group I had any surviving xenografts. Thus, xenograft survival rate was significantly improved by pretreatment with 25 ng/ml BPD.

Figure 2A:
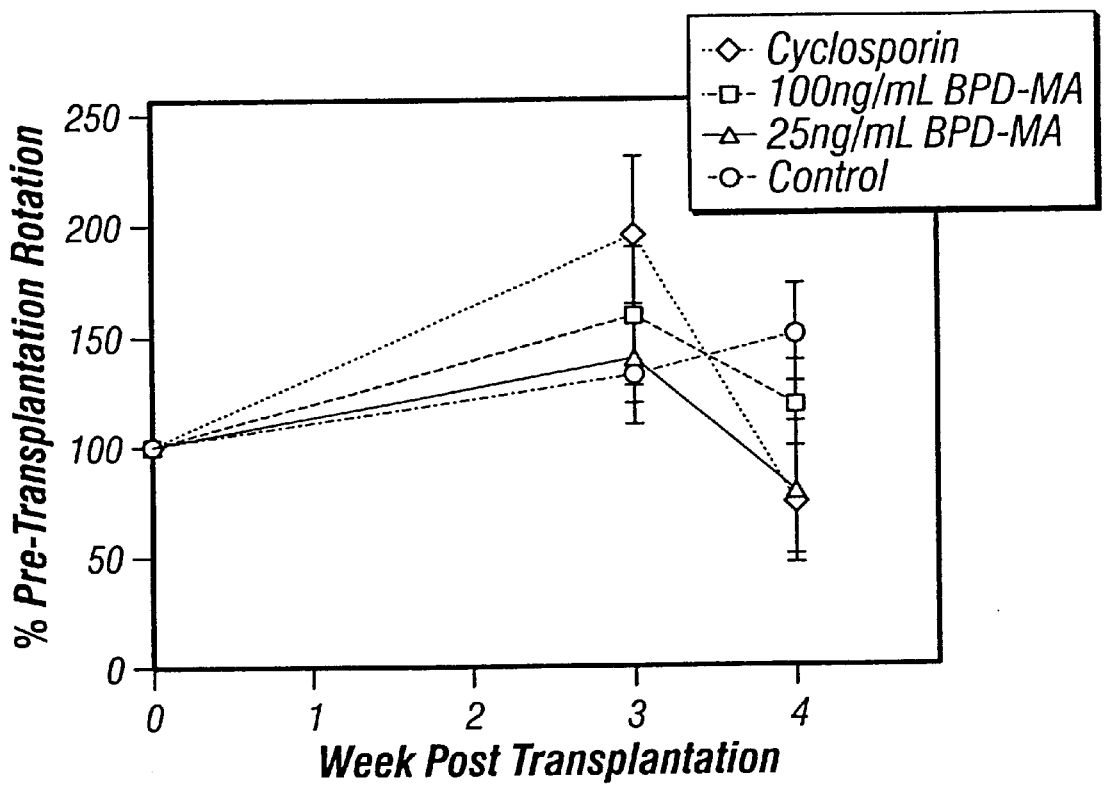
FIG. 2A records the result of a second experiment at different concentration levels of drug showing the rotational behavior of recipients over a 4-week period.
Figure 2B:
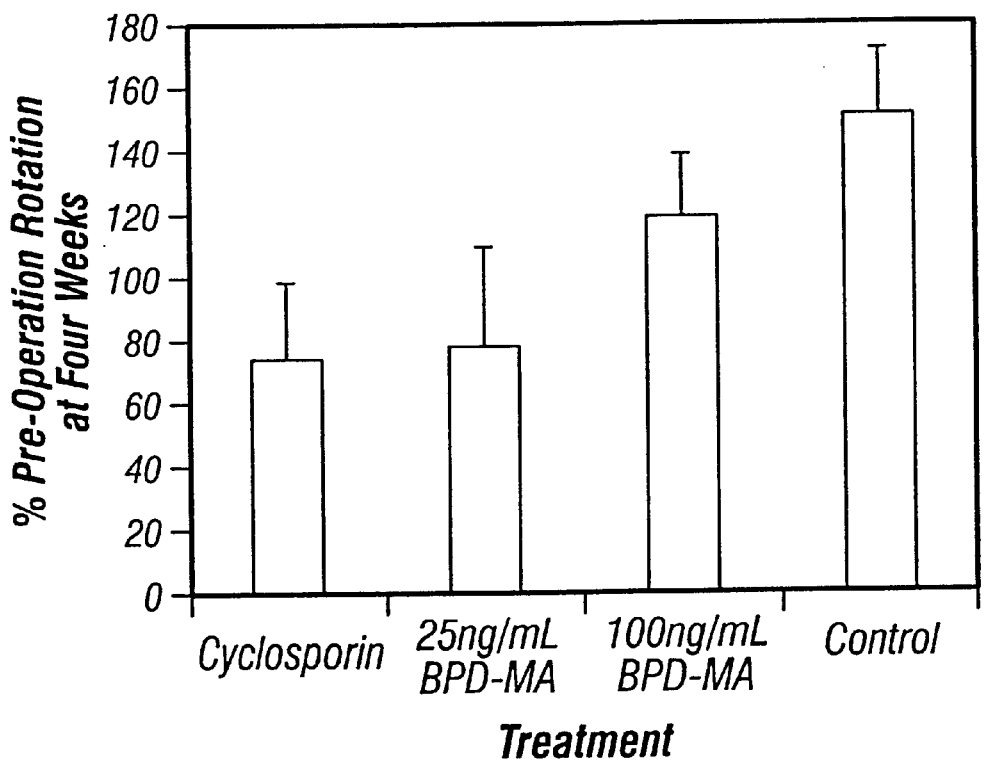
FIG. 2B is a graphic representation of this behavior at the 4-week end point.

FIG. 2A shows a graphic representation of results over a 4-week period with regard to recipients administered tissue that had been treated according to the protocol in Example 1B. Again, the solid squares represent Group I (25 ng/ml BPD-MA); the closed triangles represent Group II (100 ng/ml BPD-MA); the solid diamonds represent Group III (cyclosporin A); and the open circles represent Group IV (control). It is seen that there is a dramatic drop in rotational behavior between weeks 3 and 4 for all groups except the control. FIG. 2B shows this end-point. In this case, both cyclosporin A and 25 ng/ml BPD-MA showed lower rotational behavior than did the control.

What is claimed is:

1. A method to enhance the survival of xenogeneic donor material, which method comprises contacting donor material comprising living cells with a photosensitizer at a concentration and for a time effective to photosensitize said material;

irradiating said photosensitized material with radiation at a wavelength absorbed by the photosensitizer for a time and at an intensity to provide sufficient total energy to enhance the survival of said material in a recipient while maintaining viability of said living cells, thus modifying said donor material so as to enhance its survival time in a xenogeneic recipient, wherein the concentration of the photosensitizer, the intensity of the radiation, and the total energy provided are adjusted to provide said donor material with low-dose photodynamic therapy.

2. The method of claim 1 wherein said irradiating and contacting steps are performed simultaneously.

3. The method of claim 1 wherein said irradiating step is conducted subsequent to the contacting step.

4. The method of claim 1 which further comprises transplanting said modified donor material into a xenogeneic recipient.

5. The method of claim 1 wherein the donor material consists essentially of a cell suspension.

6. The method of claim 5 wherein said cell suspension is of neural cells.

7. The method of claim 5 wherein the cell suspension of pancreatic islet cells.

8. The method of claim 5 wherein the cell suspension comprises bone marrow cells.

9. The method of claim 1 wherein the donor material is an organ.

10. The method of claim 1 wherein the donor material is derived from a nonhuman mammal.

11. The method of claim 4 wherein the donor material is derived from a nonhuman mammal and the recipient is a human.

12. The method of claim 11 wherein said recipient has been diagnosed with a disease of the central nervous system.

13. The method of claim 12 wherein said disease is Parkinson's disease.

14. The method of claim 1 wherein the photosensitizer is a porphyrin derivative.

15. The method of claim 14 wherein the porphyrin derivative is porfimer sodium or a green porphyrin.

16. The method of claim 15 wherein the green porphyrin is BPD-MA.

* * * * *